US012569540B2

(12) United States Patent
Rodríguez Obaya et al.

(10) Patent No.: US 12,569,540 B2
(45) Date of Patent: Mar. 10, 2026

(54) HUMAN RECOMBINANT HYPOSIALYLATED ERYTHROPOIETIN, METHODS OF PURIFICATION AND THERAPEUTIC USES THEREOF

(71) Applicant: Centro De Inmunología Molecular, Havana (CU)

(72) Inventors: Teresita De Jesus Rodríguez Obaya, Havana (CU); Daniel Enrique Amaro González, Havana (CU); Judey Aymed García Artalejo, Havana (CU); Iliana Maria Sosa Testé, Havana (CU); Yanara Sarmiento Conde, Havana (CU); Lourdes Hernández De La Rosa, Havana (CU); Dayli Díaz Goire, Havana (CU); Estela Giménez López, Barcelona (ES)

(73) Assignee: CENTRO DE INMUNOLOGIA MOLECULAR, Havana (CU)

( * ) Notice: Subject to any disclaimer, the term of this patent is extended or adjusted under 35 U.S.C. 154(b) by 1025 days.

(21) Appl. No.: 17/640,133

(22) PCT Filed: Feb. 19, 2020

(86) PCT No.: PCT/CU2020/050001
§ 371 (c)(1),
(2) Date: Mar. 3, 2022

(87) PCT Pub. No.: WO2021/043345
PCT Pub. Date: Mar. 11, 2021

(65) Prior Publication Data
US 2022/0305084 A1 Sep. 29, 2022

(30) Foreign Application Priority Data
Sep. 5, 2019 (CU) .................................. 2019-0077

(51) Int. Cl.
| | |
|---|---|
| *A61K 38/18* | (2006.01) |
| *A61K 47/18* | (2017.01) |
| *A61K 47/22* | (2006.01) |
| *A61K 47/38* | (2006.01) |
| *A61P 25/28* | (2006.01) |

(52) U.S. Cl.
CPC ........ *A61K 38/1816* (2013.01); *A61K 47/183* (2013.01); *A61K 47/22* (2013.01); *A61K 47/38* (2013.01); *A61P 25/28* (2018.01)

(58) Field of Classification Search
None
See application file for complete search history.

(56) References Cited

U.S. PATENT DOCUMENTS
2004/0122216 A1 6/2004 Nielsen et al.

FOREIGN PATENT DOCUMENTS

| | | |
|---|---|---|
| EP | 1997483 A1 | 12/2008 |
| WO | 2004003176 A2 | 1/2004 |
| WO | 2005063808 A1 | 7/2005 |
| WO | 2007009404 A1 | 1/2007 |

OTHER PUBLICATIONS

Watson, Eric, et al., "Structure Determination of the Intact Major Sialylated Oligosaccharide Chains of Recombinant Human Erythropoietin Expressed in Chinese Hamster Ovary Cells," Glycobiology, vol. 4, No. 2, pp. 227-237 (1994).

Egrie, Joan C., et al., "Development and Characterization of Novel Erythropoiesis Stimulating Protein (NESP)," British Journal of Cancer, vol. 84, No. 1, pp. 3-10 (2001).

Goldwasser, Eugene,, et al., "On the Mechanism of Erythropoietin-Induced Differentiation: XIII. The Role of Sialic Acid in Erythropoietin Action," Journal of Biological Chemistry, vol. 249, No. 13, pp. 4202-4206 (1974).

Sakanaka, Masahiro, et al. "In Vivo Evidence that Erythropoietin Protects Neurons from Ischemic Damage," Proceedings of the National Academy of Sciences, vol. 95, No. 8, pp. 4635-4640 (1998).

Maiese, Kenneth, et al., "Erythropoietin in the Brain: Can the Promise to Protect be Fulfilled?" Trends in Pharmacological Sciences, vol. 25, No. 11, pp. 577-583 (2004).

Leist, Marcel, et al. "Derivatives of Erythropoietin that are Tissue Protective but not Erythropoietic," Science, vol. 305, No. 5681, pp. 239-242 (2004).

García-Rodrigues, et al., "The Nasal Route as a Potential Pathway for Delivery of Erythropoietin in the Treatment of Acute Ischemic Stroke in Humans," The Scientific World Journal, vol. 9, pp. 970-981 (2009).

Mancera-Arteu, Montserrat, et al. "Identification and Characterization of Isomeric N-Glycans of Human Alfa-Acid-Glycoprotein by Stable Isotope Labelling and ZIC-HILIC-MS in Combination with Exoglycosidase Digestion," Analytica Chimica Acta, vol. 940, pp. 92-103 (2016).

Giménez, Estela, et al. "Quantitative Analysis of N-Glycans from Human Alfa-Acid-Glycoprotein Using Stable Isotope Labeling and Zwitterionic Hydrophilic Interaction Capillary Liquid Chromatography Electrospray Mass Spectrometry as Tool for Pancreatic Disease Diagnosis," Analytica Chimica Acta, vol. 866, pp. 59-68 (2015).

(Continued)

*Primary Examiner* — Lianko G Garyu
*Assistant Examiner* — Tara L Martinez
(74) *Attorney, Agent, or Firm* — Hoffmann & Baron, LLP

(57) ABSTRACT

The present invention relates to the fields of Biotechnology and Medicine and describes a pharmaceutical composition of recombinant human erythropoietin which is characterized by having a microheterogeneity of fucosylated N-glycans formed by bi, tri and tetra-antennary structures with mono and bi-sialylated sialic acid residues that represent 40-60% of the total glycans, trisialylated ones that represent 40-43% of the total glycans and tetrasialylated ones that represent 10-13% of the total glycans. This glycosylation pattern confers properties to said composition that allow for its use in disorders of the nervous system. The method of obtaining the pharmaceutical composition described herein is also described.

6 Claims, 9 Drawing Sheets

(56) References Cited

OTHER PUBLICATIONS

Giménez, Estela, et al. "Capillary Electrophoresis Time-of-Flight Mass Spectrometry for a Confident Elucidation of a Glycopeptide Map of Recombinant Human Erythropoietin," Rapid Communications in Mass Spectrometry, vol. 25, No. 16, pp. 2307-2316 (2011).

Pedroso, Ivonne, et al. "Protective Activity of Erythropoyetine in the Cognition of Patients with Parkinson's Disease," Behavioral Sciences, vol. 8, No. 5, pp. 51 (2018).

Yuen, Chun-Ting, et al. "Relationships Between the N-Glycan Structures and Biological Activities of Recombinant Human Erythropoietins Produced Using Different Culture Conditions and Purification Procedures," British Journal of Haematology, vol. 121, No. 3, pp. 511-526 (2003).

Elliott, Steve, et al. "Structural Requirements for Additional N-Linked Carbohydrate on Recombinant Human Erythropoietin," Journal of Biological Chemistry, vol. 279, No. 16, pp. 16854-16862 (2004).

Nagai, Atsushi, et al. "Erythropoietin and Erythropoietin Receptors in Human CNS Neurons, Astrocytes, Microglia, and Oligodendrocytes Grown in Culture," Journal of Neuropathology & Experimental Neurology, vol. 60, No. 4, pp. 386-392 (2001).

Sirén, Anna-Leena, et al. "Erythropoietin Prevents Neuronal Apoptosis After Cerebral Ischemia and Metabolic Stress," Proceedings of the National Academy of Sciences, vol. 98, No. 7, pp. 4044-4049 (2001).

Lanfranco, F., "Use of Performance-Enhancing Endocrine Drugs (Doping) in Competitive and Recreational Sports Activity," Sports Endocrinology, Front Horm Res. Basel, Karger, vol. 47, pp. 115-127 (2016). (DOI: 10.1159/000445174).

Viviani, Barbara, et al. "Erythropoietin Protects Primary Hippocampal Neurons Increasing the Expression of Brain-Derived Neurotrophic Factor," Journal of Neurochemistry, vol. 93, No. 2, pp. 412-421 (2005).

Kahn, Kenneth, "The Natural Course of Experimental Cerebral Infarction in the Gerbil," Neurology, vol. 22, No. 5, p. 510 (1972). (DOI: 10.1212/WNL.22.5.510).

(A)

1. IP Standard
2. Control
3. Basic EPO 1
4. Basic EPO 2

(B)

1. 35°C pH 7,5
2. 35°C pH 7,2
3. 35°C pH 7,3
4. 37°C pH 7,3
5. 37°C pH 7,2
6. 37°C pH 7,5
7. Control Condition 1   Condition 2   Condition 3   Condition 4

Q (mg hrEPO/mL gel                    Q (mg hrEPO/mL monolith

1. RM hrEPO

2. Elution of batch 1

3. Elution of batch 2

4. Elution of batch 3

5. Elution of batch 4

A)

B)

time (min)

time (min)

A)

time (min)

B)

time (min)

HUMAN RECOMBINANT HYPOSIALYLATED ERYTHROPOIETIN, METHODS OF PURIFICATION AND THERAPEUTIC USES THEREOF

CROSS-REFERENCE TO RELATED APPLICATIONS

This application is a National Stage Application that claims a benefit of priority from Application No. PCT/CU2020/050001 filed Feb. 19, 2020, which claims priority to Application No. CU 2019-0077, filed Sep. 5, 2019, the disclosures of which are herein incorporated in their entirety.

SCOPE OF THE TECHNIQUE

The present invention relates to the fields of Biotechnology and Medicine, especially to the obtainment of a pharmaceutical composition of recombinant human erythropoietin with a glycosylation pattern that confers to it with properties that allow for its use in disorders of the nervous system.

BACKGROUND

Erythropoietin (EPO) is a glycoprotein hormone formed by 166 amino acids that has a molecular weight of 30.4 kDa (Lanfranco, F and Strasburger, C. J. (2016) Sports Endocrinology 47: 115-27). EPO is naturally produced in the perisinusoidal cells of the liver in the fetal and the perinatal period and in adulthood predominantly in the interstitial fibroblasts of the kidneys. This hormone stimulates the production of red blood cells in the bone marrow and plays an important role in the response of the brain to neuronal damage (Sirén L. et al. (2001) Proc Natl Acad Sci USA 98 (7): 4044-9.

EPO is a highly glycosylated molecule and its carbohydrate portion constitutes 40% of its molecular weight. This protein contains four complex chains of oligosaccharides linked to the polypeptide chain, three of them by N-type junctions and one by an O-type junction, whose location has been well described by different authors Elliott, S. et al. (2004) The Journal of Biological Chemistry, 279(16): 16854-16862; Watson et al. (1994) Glycobiology 4(2): 227-237. Oligosaccharides with N-type junctions can contain a variable number of sialic acid terminal residues and are critical for secretion, molecular stability, receptor binding and in vivo activity (Egrie, J. and Browne, J. (2001) Br. J. Cancer, 84(I): 3-10; Goldwasser et al. (1974) J. Biol. Chem 249: 4202-4206).

Throughout the nineties in last century up to the present, a large number of evidences on the neuroprotective properties of recombinant human EPO (rhEPO) has been accumulated. In 1998 Sakanara and colleagues in a model of global ischemia in gerbils, demonstrated that after the occlusion of the common carotid artery, rhEPO supply through the lateral ventricles resulted in a reduction of ischemic damage on hippocampal neurons in CA1 area (Sakanara, M. et al. (1998) Proc. Natl. Acad. Sci. USA, 95: 4635-4640).

The cytoprotective effects of EPO on the central nervous system have been demonstrated by Maiese and colleagues in 2004 and later by Viviani and colleagues in 2005. (Maiese, K. et al. (2004) Trends in Pharmacological Sciences 25 (11): 577-83; Viviani, D. et al. (2005) Journal of Neurochemistry 93 (2): 257-268). Despite all the information accumulated in non-clinical studies on hematopoietic EPO, the results achieved have not been reproduced in the clinic, due to the adverse events associated to its prolonged use that occur in patients.

In adults, the expression of the EPO receptor in the nervous system is found mainly in neurons, astrocytes and microglia, while astrocytes produce EPO, this is a hyposyallylated EPO (Nagai, A. et al. (2001) Journal of Neuropathology & Experimental Neurology, 60 (4): 317-319.

A significant number of researchers have undertaken the task of modifying rhEPO to achieve a drug that has the same neuroprotective properties but without the adverse events caused by the hematopoietic action. The EPO called AsialoEPO (US 2004/0122216) which is obtained by means of a total enzymatic desialylation of rhEPO has the desired properties mentioned above, this kind of EPO has a high affinity for the rhEPO receptor but a limited protective action due to a plasma half-life extremely short. Another example of modification of erythropoietin is the transformation of lysine into homocitrulline by the carbamylation of the protein that results in a carbamylated EPO called CEPO (Leist, M., Ghezzi, P., Grasso, G., et al. (2004) 305 (5681): 239-242). Although both EPOs showed no hematopoietic effect, in clinical trials conducted with CEPO, even if no adverse effects were observed, neuroprotective effectiveness was not demonstrated.

Patent application WO 2007/009404 claims different nasal formulations of an EPO with low sialic acid content, later called NeuroEPO in a publication of its authors (Garcia, J C and Sosa, I. (2009), The Scientific World Journal, 9: 970-981.) This rhEPO is obtained by a hollow fiber membrane fermentation process and ion exchange chromatography in the purification to separate the most acidic isoforms (those that have a higher sialic acid content from those with less sialic acid content). Said NeuroEPO has a profile of 13 isoforms, of which it shared 9 with the hematopoietic rhEPO called EPOCIM®.

For the first time, the authors of the present invention describe a production process in a stirred tank (ST) combined with a purification step carried out by means of a chromatography using a monolithic column as an anion exchanger with a quaternary ammonium ligand Q, capable of increasing the expression of rhEPO hyposialylated isoforms without additional chemical and genetic modifications. These isoforms have an isoelectric point profile in a pH range between 4.25 and 5.85 and a tertiary structure associated with glycosylation different from that of NeuroEPO that gives them greater effectiveness in neuroprotection and neuro-restoration mechanisms both in vitro and in vivo.

BRIEF DESCRIPTION OF THE INVENTION

In one embodiment, the object of the present invention is a pharmaceutical composition characterized in that it comprises as active principle an rhEPO with an isoform profile whose isoelectric point in the range between 4.25 and 5.85. Said rhEPO has a microheterogeneity of fucosylated N-glycans formed by bi, tri and tetra-antennary structures, which have mono and bi-sialylated sialic acid residues that represent between 40-60% of the total glycans, trisialylated ones that represent between 40-43% and tetrasialylated ones that represent between 10-13% as well as a pharmaceutically acceptable excipient.

Particularly, the O-glycosylation site in serine 126 has 3 sialoforms which have between 0 to 2 sialic acid residues, the monosialylated structure being the most abundant and representing between 78-82% of the total glycans while the asialylated structures represent between 6-10% of total glycans.

The N-glycosylation site of asparagine 83 comprises:

fucosylated biantennary structures with 1 and 2 sialic acid residues, where said structures represent between 8-12% of the total glycans, fucosylated triantennary structures with 1, 2 and 3 sialic acid residues where these structures represent 17-21% of the total glycans, fucosylated tetraantennary structures, which have from 1 to 4 sialic acid residues, where these structures represent 27-31% of the total glycans and fucosylated tetraantennary structures with N-acetyl lactosamine type 1 and 2 that have from 1 to 4 sialic acid residues, these structures represent 38-42% of the total glycans.

The pharmaceutically acceptable excipients for the pharmaceutical composition claimed in the present invention include but are not limited to bioadhesive polymers such as hydroxypropyl methylcellulose, and protein stabilizers such as L-tryptophan, L-leucine, L-arginine hydrochloride and L-histidine hydrochloride.

The above-described structure of the rhEPO isoforms that are part of the pharmaceutical compositions object of the present invention confers them with greater effectiveness in neuroprotection and neuro-restoration mechanisms both in vitro and in vivo.

In another embodiment, the object of the present invention is a method for obtaining an unmodified rhEPO where the fermentation process takes place in ST in perfusion mode at a temperature range of 34±2° C., with a culture medium free of proteins and pH range from 7.2 to 7.3, this medium is supplemented with glutamine until a final concentration of 8-12 mmol/L is obtained. This method also comprises a purification process that has a chromatographic step in which a monolithic column is used as an anion exchanger with a Q quaternary ammonium ligand, the equilibrium buffer being a 20 mmol/L Tris 10 mmol/L HCl solution whose pH is in the range from 7.9 to 8.10, with conductivity range from 1.35-1.65 mS/cm and that uses a 50 mmol/L sodium acetate elution buffer with pH from 4.3 to 4.5 and conductivity from 2 to 3.5 mS/cm.

With the method described in the present application, a pharmaceutical composition with increased number of low sialic acid content isoforms that have a tertiary structure associated with glycosylation different from that of NeuroEPO, which confers them with greater effectiveness in neuroprotection and neuro-restoration mechanisms both in vitro and in vivo.

It is also the object of the present invention the use of the pharmaceutical composition described herein for the treatment of dementia, stroke, parkinson's disease, ataxia, craniocerebral trauma, glaucoma, autism, hypoxia of the newborn, multiple sclerosis, amyotrophic lateral sclerosis and neurological damage induced by trauma, poisoning or radiation. Particularly, a method for the treatment with this pharmaceutical composition of a subject in need of such treatment is described, where the administration of said composition is performed from one to three times per week in periods of time from 6 to 12 months in an administration range from 0.1 mg to 4 mg in a volume of 1 mL.

DETAILED DESCRIPTION OF THE INVENTION

Pharmaceutical Compositions

The rhEPO object of the present invention is characterized in that it has an isoelectric point profile between 4.25 and 5.85 and a secondary and tertiary protein structure not associated with glycosylation similar to rhEPO maintaining the same tertiary structure associated with glycosylation with an O-glycosylation site in Serine 126 and three N-glycosylation sites in Asparagine 24, 38 and 83. The carbohydrate composition of the rhEPO described herein differentiates it from other rhEPO. The microheterogeneity of fucosylated N-glycans is comprised of bi, tri and tetraantennary structures that have mono and bi-sialylated sialic acid residues in a range between 40-60% of total carbohydrates, preferably in a range between 43-50%, trisialylated ones in a range between 40-43% and tetrasialylated ones in a range between 10-13% of total carbohydrates.

Particularly, the O-glycosylation site in serine 126 has 3 sialoforms that have between 0 to 2 sialic acid residues, the monosiallylated structure is the most abundant and represents between 78-82% of the total glycans and the asialylated structures represent 6-10% of total glycans.

The N-glycosylation site of asparagine 83 comprises:

fucosylated biantennary structures with 1 and 2 sialic acid residues, where said structures represent 8-12% of the total glycans, fucosylated triantennary structures with 1, 2 and 3 sialic acid residues where these structures represent 17 to 21% of the total glycans, fucosylated tetraantennary structures, which have between 1 and 4 sialic acid residues, where these structures represent 27-31% of the total glycans and fucosylated tetraantennary structures with N-acetyl lactosamine type 1 and 2 which have between 1 to 4 sialic acid residues, where these structures are in a range between 38-42% of the total glycans.

The terms hyposialylated rhEPO, EPO, HS or basic isoforms are used interchangeably in the present invention to refer to the pharmaceutical compositions having the characteristics described above, also commonly referred to as NeuroEPO plus.

The pharmaceutical compositions object of the present invention have as active ingredient hyposialylated isoforms of rhEPO. These hyposialylated isoforms are obtained through the process described in the present invention, which does not imply the chemical and/or genetic modification of the rhEPO to obtain said isoforms. The rhEPO isoforms that are part of the active principle of said pharmaceutical compositions have a tertiary structure associated with glycosylation different from that of the NeuroEPO, which confers them with greater effectiveness in neuroprotection and neuro-restoration mechanisms both in vitro and in vivo.

The pharmaceutical compositions object of the present invention are administered by the nasal or ophthalmic administration routes and are in the form of aqueous solutions whose finished dosage forms are nasal drops, nasal sprays or eye drops. Said pharmaceutical formulations comprise the hyposialylated rhEPO as active ingredient and optionally pharmaceutically suitable excipients and/or stabilizers.

Pharmaceutically acceptable excipients and/or stabilizers are non-toxic to subjects who receive them at the doses and concentrations employed and may include bioadhesive polymers such as hydroxymethylcellulose, hydroxypropylcellulose and methylcelluose; protein stabilizers such as L-tryptophan, L-leucine, L-arginine hydrochloride and/or L-histidine hydrochloride and its salts.

Therapeutic Application and Treatment Methods

The present invention provides pharmaceutical compositions useful in the treatment of nervous system disorders such as: cerebrovascular, psychiatric and neurodegenerative diseases. Particularly, said diseases can be: dementia, stroke, Parkinson's disease, ataxia, craniocerebral traumas, glaucoma, autism, hypoxia of the newborn, multiple sclerosis, amyotrophic lateral sclerosis and neurological damage induced by trauma, poisoning or radiation.

The invention further provides a method comprising the administration of hyposialylated rhEPO to a subject in need of such treatment from one to three times per week in periods from 6 to 12 months. Said administration will be carried out intranasally (IN), slowly, by instillation of the drug in the mucose. The administration dose being in the range between 0.1 mg-4 mg, preferably between 0.5 mg-1 mg. The maximum administration volume per dose is 1 mL; 0.5 mL per nostril for a total daily dose of 3 mL. Said volume can be distributed in smaller volumes at time intervals of 5-15 minutes between each application, preferably every 15 minutes.

Method for Obtaining the Hyposialylated Isoforms of rhEPO

The method claimed in the present invention is composed of different stages and employs the cell lines described below:

Cell Lines

The cell lines that can be used to perform the method object of the present invention are the same reported for the production of rhEPO. Among the lines most used are: CHO, COS, BHK, Namalwa, HeLa, Hep3B, HepG2, preferably for the present invention the CHO cell line is used.

Fermentation Process

The fermentation process of the present invention is performed using ST technology. This process consists of several stages, the first one comprises the defrosting of an ampule from a working cell bank until reaching room temperature (18-24° C.). Subsequently, an expansion stage is performed where the cells are scaled to a cell concentration and cell viability that ensures the proper inoculation of the seed fermenter with the objective of increasing the biomass.

Once a cell density of a 1×106 cells/mL is reached, the fermentation is started with different modes of operation. These modes can be: batch cultivation, continuous cultivation with or without biomass retention.

In order to obtain the hyposialylated isoforms a temperature in the range of 34±2° C. and pH in the range of 6.8±0.4 should be ensured at this stage of fermentation.

The cells should grow in a protein-free culture medium until obtaining a final concentration of glutamine in the range of 8-12 mmol/L.

Purification Process

The process of purification of the hyposialylated rhEPO comprises the following chromatographic steps:

First, a pseudo-affinity chromatography in colored ligand is performed. The objective of this step is the capture of rhEPO and the partial removal of the main contaminants present in the supernatant (SN). Subsequently a gel filtration chromatography is carried out to change the buffer of the protein to that of the application solution for the next chromatographic step.

Then a pseudo-affinity chromatography by metal chelates is performed. This step aims at capturing rhEPO and totally eliminating the fraction of contaminants that were not removed in the previous steps of the process. A gel filtration chromatography is carried out again to change the buffer to that of the application solution of the next chromatographic step.

As a critical stage of the production process, an anion exchange chromatography with Q quaternary ammonium ligand is performed. In this chromatographic step, monolithic columns are used. The objectives of this chromatography are the separation of the hyposialylated (biologically active) isoforms from the acid ones, the retention of DNA and the concentration of the product. All of which guarantees that hyposialylated isoforms without contamination or mixing with the acidic isoforms are obtained.

Finally, a gel filtration chromography is performed again with the objective of changing the buffer and allowing the protein to elute in the form of active raw material.

The present invention is further elaborated with the following examples and figures. However, these examples are not meant to be construed as limiting the scope of the invention.

EXAMPLES

Example 1. The pH and Temperature Influence rhEPO Isoform Profile at Laboratory Scale From the CHO cell line transfected with the human EPO gene, a seed cell bank was obtained which was adapted to grow in suspension in a protein-free medium. The complete adaptation to this culture medium was obtained after 37 generations representing 25 days of cultivation.

To evaluate the performance of the cell line in the presence of different pH and temperature conditions, an experimental design was carried out where both variables were combined. The experimental conditions are shown in Table 1. The pH of the culture was controlled with the addition of 0.5 mol/L sodium hydroxide.

TABLE 1

Experimental conditions to evaluate the influence of pH and temperature variables on the rhEPO isoform profile.

| | |
|---|---|
| Initial cell concentration (cell/mL) | $0.3 \times 10^6$ |
| Cell viability (%) | >90 |
| Culture time (days) | 7 |
| Incubation temperature (° C.) | 35 |
| | 37 |
| Work volume (mL) | 300 |
| pH | 7.2 |
| | 7.3 |
| | 7.5 |

The isoform profile of rhEPO corresponding to the samples of SN generated in the cultures in the different conditions evaluated was determined by isoelectric focusing. A mixture of ampholins with a pH range from 2 to 5 and from 3 to 10 was used, an internal EPOCIM® reference material was used as control. The intensity percentage of each of the isoforms in the samples was analyzed by densitometry, using the *Gene Tools* program. Isoforms with pH values ranging from 2.80 to 4.25 were defined as acidic isoforms and the ones with pH values in the range from 4.25 to 6.55 as basic isoforms (FIG. 1A).

Figure 1:
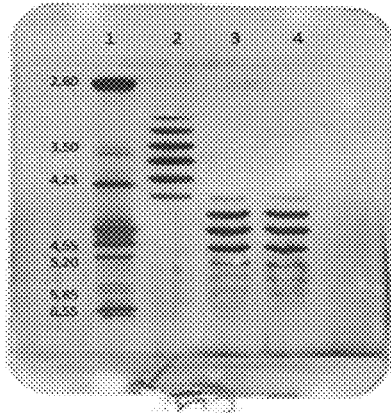
FIG. 1. Isoform profile: A) Definition of cut of the isoforms; B) SN generated in the cultures under the conditions of temperature and pH evaluated.
Figure 1:
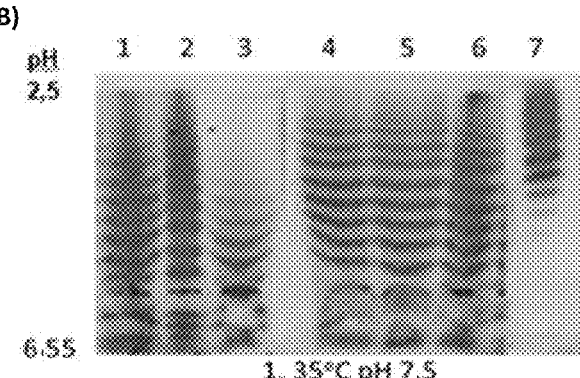

FIG. 1B shows that the isoform profile was strongly influenced by temperature. Regardless of pH, when the SN samples corresponding to each condition were compared at a temperature of 37° C. with the control, the 7 acid isoforms are observed. On the other hand, at 35° C. a loss of acidic isoforms was observed, which was more pronounced in the conditions with pH 7.2 and 7.3.

Figure 2:
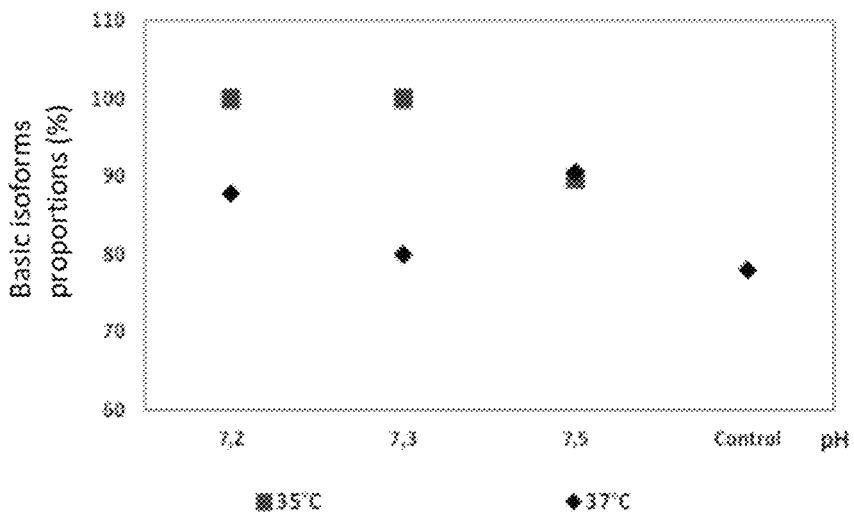
FIG. 2. Proportion of hyposialylated isoforms in the cultures under the temperature and pH conditions evaluated.

FIG. 2 shows that under the conditions of pH 7.2 and 7.3 and temperature 35° C., the total of the isoforms obtained (100%) were basic isoforms.

Example 2. The pH and Temperature Influence rhEPO Isoform Profile at Pilot Scale The impact of the best culture conditions obtained at laboratory scale (Temperature 35° C., pH 7.2 and 7.3) in a more controlled and favorable environment for the cell culture was evaluated. From the seed cell bank described in Example 1, four fermentation runs were designed using a ST type bioreactor (Infors-AGCH 4103, Bottmingen) of 3.5 L effective volume. The operating conditions are shown in Table 2. Initial cell viability was greater than 90% in all the conditions evaluated.

TABLE 2

Operating conditions corresponding to each fermentation run.

| Parameters | Condition 1 | Condition 2 | Condition 3 | Condition 4 |
|---|---|---|---|---|
| Initial Xv (cell/mL) | $0.5 \times 10^6$ | $1.76 \times 10^6$ | $1.08 \times 10^6$ | $2.31 \times 10^6$ |
| Operation temperature (° C.) | 37 | 35 | 35 | 37 |
| pH | 7.41 | 7.2 | 7.3 | - |
| Work volume (L) | 1.5 | 3 | 3 | 3 |
| Total cultivation time (days) | 5 | 7 | 7 | 7 |
| Air flow (mL/min) | 15 | 15 | 15 | 15 |
| Rotational impeller speed (rpm) | 150 | 150 | 150 | 150 |
| Dilution rate (vvd) | — | 0.3 | 0.3 | 0.3 |

Figure 3:
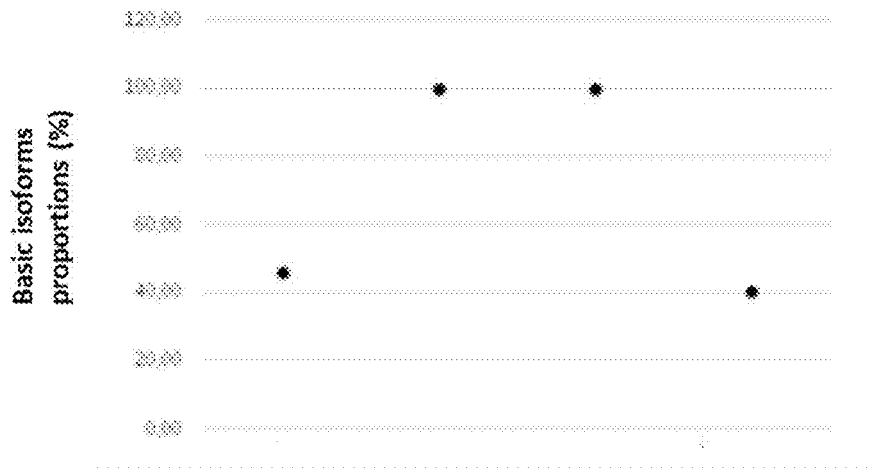
FIG. 3. Proportion of hyposialylated isoforms in each culture under the conditions evaluated at pilot scale.

Samples were taken at the end of each fermentation and the isoform profile of the SN samples generated in the cultures for the conditions evaluated in the bioreactor was determined by means of the isoelectric focusing technique. Once these profiles were obtained, Gene Tools program was used and starting from the image corresponding to the isoelectric focusing gel, the intensity of each band present in the gel was determined and the proportion of the hyposialylated isoforms for each condition was evaluated. As can be seen in FIG. 3 in culture conditions 2 and 3 (35° C., pH 7.2-7.3), the proportion of hyposialylated isoforms was higher than in conditions 1 and 4. These results corroborate the findings obtained at laboratory scale, that is, that by modifying the operating conditions to have a pH 7.2-7.3 and a temperature of 35° C., the isoform profile of rhEPO is modified, a greater intensity being achieved in those with pH values between 4.25 and 5, 85.

Example 3. By Increasing the Concentration of Glutamine in the Culture Medium, the Expression of rhEPO Basic Isoforms is Favored In order to assess whether the increase in the concentration of glutamine in the culture medium had an effect on the increase in hyposialylated isoforms, the performance of the rhEPO-producing CHO cell line was evaluated. A seed cell bank which was exposed to different glutamine concentrations of the culture medium was used, and an adaptation to the culture medium was carried out for 15 days. The assessment started with an initial cell concentration of $0.5 \times 10^6$ cel/mL in a final volume of 300 mL of culture medium, using rotating bottles that were kept in 37° C. incubators with an agitation speed of 600 rpm.

The final glutamine concentrations in the culture medium were: 8, 12 and 16 mmol/L and a culture medium with 6 mmol/L of glutamine was used as control.

The relative intensity of hyposialylated isoforms in the SN of the cultures was evaluated by densitometry after seven days of treatment with the different concentrations of glutamine.

Figure 4:
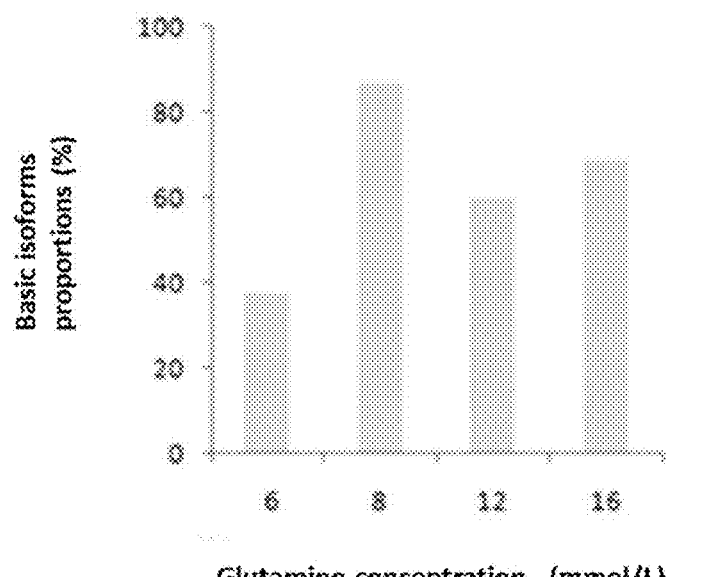
FIG. 4. Relative intensity of less acidic isoforms in the SN.

FIG. 4 shows that with each of the three variants evaluated a higher proportion of hyposialylated isoforms was obtained with respect to the control, thus corroborating that with an increase in the concentration of glutamine in the culture medium, the obtainment of hyposialylated isoforms in the SN is favored. The highest value of these isoforms was observed with 8 mmol/L of glutamine (87%).

Example 4. The pH and Conductivity Influence the Adsorption of the Acidic and Basic Isoforms in the Q Strong Quaternary Ammonium Anion Exchanger at a Laboratory Scale With the objective of determining the pH and conductivity conditions that favor the greatest adsorption of acidic isoforms in the Q strong quaternary ammonium anion exchanger the following buffer solutions were evaluated: 20 mmol/L sodium phosphate (anhydrous dibasic and monobasic dihydrate) and 20 mmol/L Tris 10 mmol/L HCl. Buffer solutions were studied at different pH and conductivity values, pH between 6 and 8 and conductivity between 1.5 and 5 mS/cm.

Figure 5:
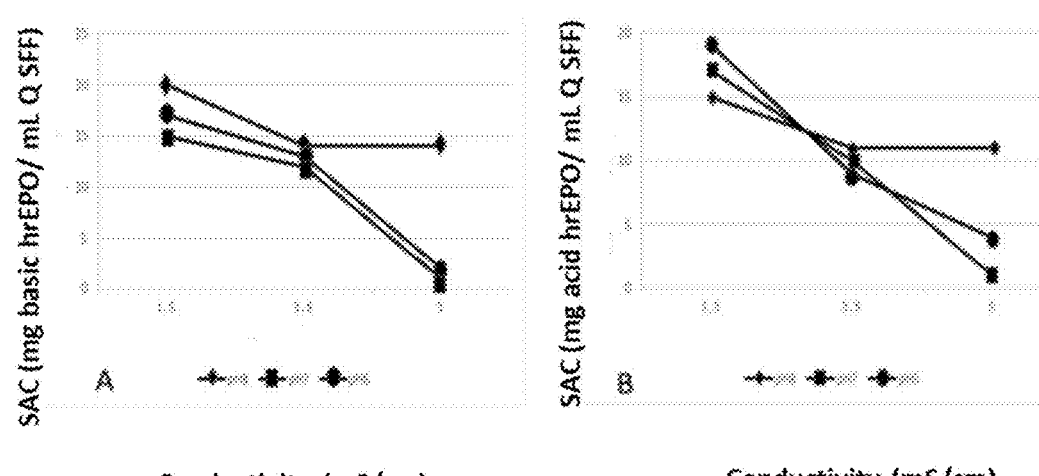
FIG. 5. Influence of mobile phase pH and conductivity on the static adsorption capacity in the Q quaternary ammonium ligand of rhEPO isoforms: (A) hyposialylated (basic), (B) acidic.

The greatest adsorption of acidic isoforms to the exchanger was observed with conditions of pH 6 and conductivity 1.50 mS/cm. On the other hand, the adsorption of the hyposialylated (basic) isoforms is maximized at pH 8 and conductivity 1.50 mS/cm. The results are shown in FIG. 5.

Example 5. Q Strong Anionic Matrix that Uses the Monolithic Column Technology has Better Performance in Terms of Capacity to Separate rhEPO Isoforms as Compared to the One that Uses the Conventional Technology of Chromatographic Gels at a Laboratory Scale The dynamic adsorption capacity (Q) of each technology under study was calculated with two breakthrough curves, using two of the linear flow rates recommended by the manufacturer of each technology 100 cm/h and 600 cm/h for the technology of chromatographic gels (Q SFF) and 156 cm/h and 624 cm/h for the monolithic column (CIM QA). The equilibrium solution used for experiments with the conventional technology and for the monolithic column technology was Tris-HCL buffer with pH 8 and conductivity 1.5 mS/cm, according to the results obtained in Example 4.

The rhEPO sample was applied to the columns and at the exit from them samples were taken at different times. The concentration of proteins (C) in each sample was determined by spectrophotometry. With the known values of C in each of the samples, the fraction of non-adsorbed protein $C/C_0$ was calculated. The load, which is the mass of protein applied to the column per unit volume of gel given in mg of rhEPO/mL of Q matrix was calculated for each time.

Figure 6:
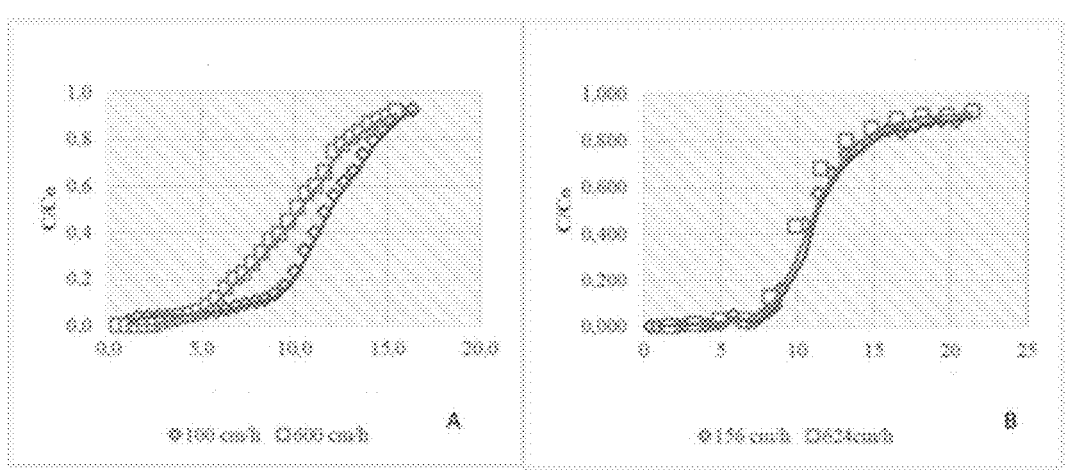
FIG. 6. Breakthrough curves A): Chromatographic matrix "Q SFF", B): Monolithic column "CIM QA".

In FIG. 6 the values of C/C0 vs. dynamic adsorption capacity are represented graphically in breakthrough curves that allow to know the Q of the gel per fraction of non-adsorbed protein $C/C_0$=0.1 at the specified flow rates. FIG. 6A shows the breakthrough curve obtained with the conventional technology of chromatographic gels where the lowest flow rate was the one with the highest dynamic capacity. FIG. 6B shows that the monolithic column has very similar dynamic adsorption capacity with the two linear flow rates tested, so it can be operated at higher flow rates, without experiencing variations in the dynamic adsorption capacity of the matrix.

Table 3 shows the Q values obtained with the different measurements performed.

TABLE 3

| Values of Q obtained with each of the flow rates studied in Q SFF and CIM QA columns. | | |
|---|---|---|
| Column | Air flow (cm/h) | Q (rhEPO/mL of gel) |
| QSFF | 100 | 7.82 |
| | 600 | 5.58 |
| CIM QA | 156 | 8.25 |
| | 624 | 7.79 |

When comparing the results of the Q studies carried out in strong anion exchangers in packed bed and the monolithic column technology, it was observed that both technologies have similar Q at the lowest linear velocity studied. However, at the highest linear velocity the monolithic column has a dynamic adsorption capacity 1.40 times greater than that of the traditional chromatographic matrix evaluated. Therefore, it can be concluded that the monolithic column allows for the increase of the work flow of the process without affecting the capacity of processing the rhEPO mass to be purified.

Example 6. By Lowering the pH, the Elution of the Hyposialylated rhEPO Isoforms in the Monolithic Column at Laboratory Scale is Favored Experimental tests were performed using Q SFF and CIM QA columns. The equilibrium solution used for both technologies was the Tris-HCl buffer at pH 8 and conductivity of 1.5 mS/cm, according to Example 4. The working linear velocity of the Q SFF column was 600 cm/h and that of the monolithic column was 624 cm/h. The product used for the experiments was the one obtained from the "Sephadex" G-25 molecular exclusion chromatographic column, after the change of buffer to that of equilibrium solution mentioned above was carried out. For the elution of the basic isoforms several runs were performed with the monolithic anion-exchange column using the 50 mmol/L Tween 20 sodium acetate buffer at 0.01% with pH values: 4.41; 4.81; 5.06; 5.20.

Figure 7:
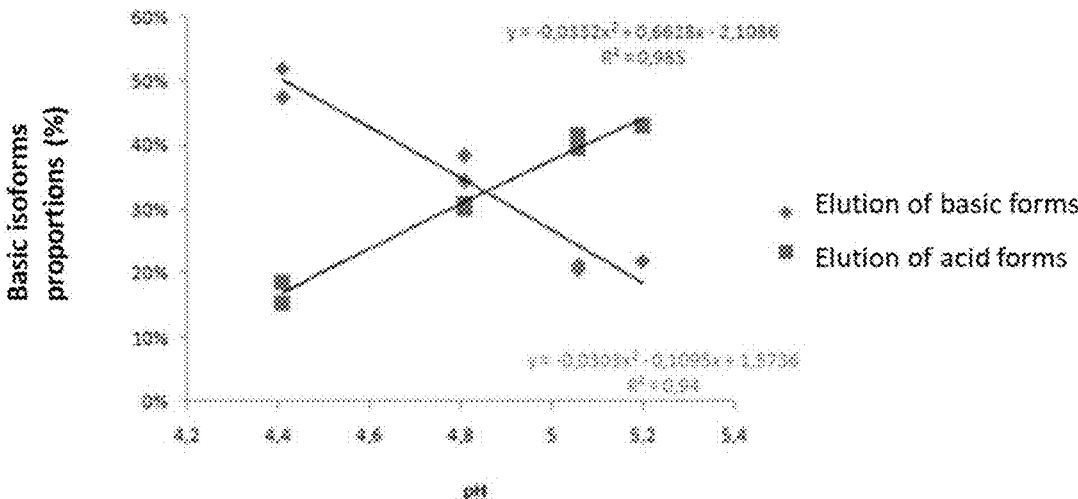
FIG. 7. Influence of elution buffer pH on the performance of basic and acidic isoforms.

The recoveries obtained in the elution of the hyposialylated (basic) isoforms and the acidic isoforms in each run are shown in FIG. 7. From the analysis of these results it was determined that as the pH of the elution buffer solution of basic isoforms increases their performance decreases, therefore the 50 mmol/L sodium acetate buffer at pH 4.41 was selected for the elution.

Example 7. The Process of Obtaining the Hyposialylated rhEPO at Production Scale is Consistent in Terms of Separation of Isoforms and Purity Degree From the seed cell bank described in Example 1, a fermentation run was carried out the initial cell viability being greater than 90%. The fermentation stage was performed at a temperature of 35° C., in a protein-free culture medium which was supplemented to reach a final concentration of 8 mmol/L of glutamine, the pH of the medium was kept between 7.2 and 7.3.

Once four harvests were obtained, the purification stage was performed where for the critical step the anion exchanger with Q quaternary ligand was used using a monolithic column. A Tris-HCl solution at pH 8 and conductivity of 1.5 mS/cm was used as equilibrium buffer and the 50 mmol/L sodium acetate buffer pH 4.41 was used for the elution.

Figure 8:
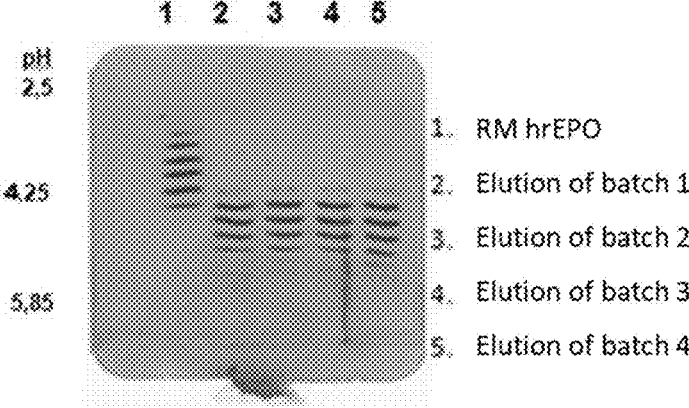
FIG. 8. Distribution of the hyposialylated isoforms of rhEPO at production scale.

The isoform profile of the four batches of active raw material obtained after the purification process was determined by means of the isoelectric focusing technique. A mixture of ampholins with a pH range from 2 to 5 and from 3 to 10 was used, and an internal EPOCIM® reference material was used as control. FIG. 8 shows the consistency in the separation of the isoforms where an isoform profile configured by six major isoforms is observed of which only two are shared with the control.

In addition, the sialic acid content of the purified isoforms was determined according to the procedure for the determination of this molecule described in Europe 8.0 Pharmacopoeia (2014) and the purity by reverse phase HPLC. Table 4 shows the sialic acid content and purity results obtained.

TABLE 4

Sialic acid content and purity results of the hyposialylated rhEPO.

| Product | Sialic Acid (sialic acid mol/mol of protein) | RP-HPLC (%) |
|---|---|---|
| Batch 1 | 5.1 | 96.24 |
| Batch 2 | 5.5 | 98.03 |
| Batch 3 | 6.5 | 98.38 |
| Batch 4 | 6.9 | 98.29 |

The content of sialic acid was less than 10 mols of sialic acid/protein molecule and the purity was greater than 95% in the four batches from which it can be concluded that the process to obtain hyposyalylated rhEPO guarantees the obtainment of isoforms in a pH range between 4.25 and 5.85, which is different from that observed in NeuroEPO.

Example 8. The Tertiary Structure Associated with Glycosylation of the Hyposialylated rhEPO Shows a Characteristic Microheterogeneity Glycan Analysis To study its N-glycans profile hyposialylated rhEPO underwent a process of denaturation and enzymatic digestion with Peptide N-glycosidase F (PNGase F). Once the N-glycans were released, they were purified by solid phase extraction using HyperSep Hypercab SPE cartridges (Mancera-Arteu, M. et al. (2016) Anal. Chim. Acta 940: 92-103.

Subsequently, they were derivatized according to the procedure described by Giménez et al. in 2015. (Gimenez, E et al. (2015) Anal. Chim. Acta, 866: 59-68).

A zwitterionic-hydrophilic interaction capillary liquid chromatography coupled to mass spectrometry was performed following the methodology described by Mancera-Arteu, M. et al. (2016) Anal. Chim. Acta, 940: 92-103.

Figure 9:
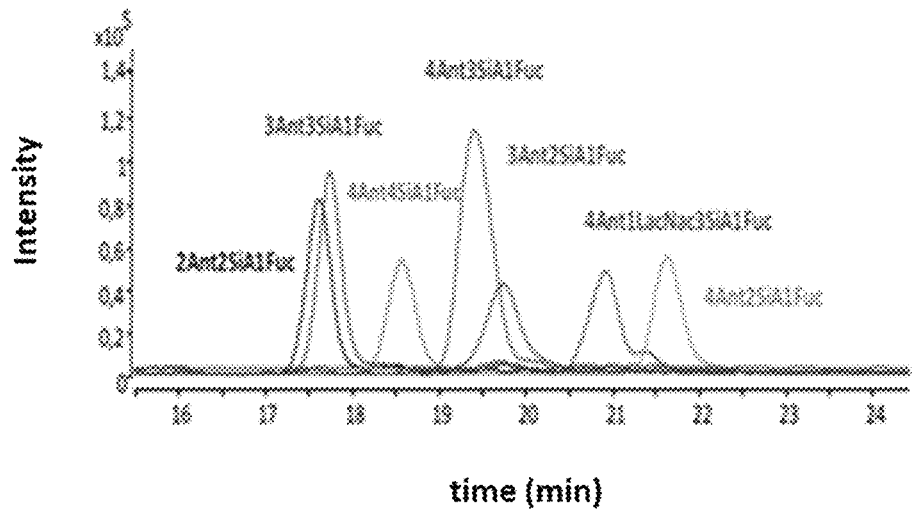
FIG. 9. Study of the N-glycans of the hyposialylated rhEPO by zwitterionic hydrophilic interaction liquid chromatography coupled to mass spectrometry.

FIG. 9 shows the mass spectra of three of the glycans detected in the hyposialylated rhEPO. As can be seen, glycan 3Ant2SiA1Fuc is the most abundant, while glycan 4Ant4SiA1Fuc is found in decreased quantities.

Table 5 shows the percentage of relative area of glycans according to structure.

TABLE 5

Percentage of relative area of glycans according to structure.

| Glycans | Area (%)** |
|---|---|
| Biantennary structures | 10.3 |
| Triantennary structures | 17.2 |
| Tetraantennary structures | 72.5 |

Table 6 shows the glycans detected with the corresponding relative areas, monoisotopic experimental molecular mass (Mexp) and mass error. As can be seen there is a significant number of glycans with less sialylated structures.

TABLE 6

N-glycans detected in the hyposialylated rhEPO by zwitterionic-hydrophilic interaction capillary liquid chromatography coupled to mass spectrometry.

| | Glycans | Area | Area (%)* | Area (%) ** | Mexp[Da] | Error |
|---|---|---|---|---|---|---|
| 2 Ant | 2Ant1SiA1Fuc | 608.586 | 2.91 | 10.3 | 2154.8011 | 9.39 |
| | 2Ant2SiA1Fuc | 2.321.812 | 11.31 | | 2445.8983 | 8.34 |
| 3 Ant | 3Ant1SiA1Fuc | 448.587 | 2.18 | 17.2 | 2519.9309 | 6.25 |
| | 3Ant2SiA1Fuc | 1.872.328 | 8.98 | | 2811.0307 | 7.25 |
| | 3Ant3SiA1Fuc | 2.562.955 | 12.46 | | 3102.1243 | 6.58 |
| 4Ant | 4Ant1SiA1Fuc | 589.168 | 2.94 | 30.1 | 28885.0669 | 8.01 |
| | 4Ant2SiA1Fuc | 2.122.871 | 10.03 | | 3176.1571 | 6.09 |
| | 4Ant3SiA1Fuc | 4.243.325 | 20.74 | | 3467.2550 | 5.60 |
| | 4Ant4SiA1Fuc | 1.575.249 | 7.80 | | 3758.2975 | 5.11 |
| 4Ant 1LacAc | 4Ant1LacNAc1SiA1Fuc | 205.545 | 1.01 | 35.0 | 3250.1917 | 5.45 |
| | 4Ant1LacNAc2SiA1Fuc | 1.506.731 | 3.67 | | 3541.2889 | 5.75 |
| | 4Ant1LacNAc3SiA1Fuc | 807.621 | 7.01 | | 3832.3847 | 3.44 |
| | 4Ant1LacNAc4SiA1Fuc | 8.539.613 | 3.00 | | 4123.4849 | 4.12 |
| 4Ant 2LacAc | 4Ant2LacNAc2SiA1Fuc | 185.318 | 0.88 | 3.32 | 3906.4126 | 1.11 |
| | 4Ant2LacNAc3SiA1Fuc | 433.265 | 2.06 | | 4197.4971 | 5.26 |
| | 4Ant2LacNAc4SiA1Fuc | 322.987 | 1.59 | | 4488.5519 | 6.33 |
| 4Ant 3LacAc | 4Ant3LacNAc1SiA1Fuc | 68.423 | 0.32 | 4.081 | 3980.5185 | 24.3 |
| | 4Ant3LacNAc2SiA1Fuc | 1.092.708 | 0.3 | | 4271.4698 | 16.70 |
| | 4Ant3LacNAc3SiA1Fuc | 83.360 | 0.38 | | 4562.5930 | 13.0 |
| | 4Ant3LacNAc4SiA1Fuc | 95.315 | 0.43 | | 4853.6515 | 16.6 |

*It represents the relative area with respect to the total of glycans detected.
** it represents the relative area grouped by antennas with respect to the total of glycans detected.

As can be seen in Table 6, glycans with more sialylated structures (four sialic acid molecules) are found in a low ratio. Instead, structures with a sialic acid molecule that have not been found in other rhEPOs such as 3Ant1SiA1Fuc, 4Ant1SiA1Fuc, 4Ant1LacNAc1SiA1Fuc and 4Ant3LacNAc1SiA1Fuc are detected. The glycan 4Ant3Sia1Fuc is abundant in the hyposialylated rhEPO. Also, it can be seen that the percentage of the relative area by antennas with respect to the total glycans detected is different from other rhEPO and that the structures with one or two sialic acid residues represent more than 50% of the relative area by antennas.

Glycopeptide Analysis

To detect all the glucoforms present in the $O_{126}$ and $N_{83}$ glycopeptides, the rhEPO and the rhEPO-CRS (pharmacopoeia reference product) were subjected to digestion with trypsin and neuraminidase (rhEPO HS-TN). All sialoforms in each glucoform detected were studied from the trypsin digestion analysis (rhEPO HS-T). The samples were analyzed by mass spectrometry according to the procedure described by Giménez, E. et al. (2011) Rapid Commun Mass Spectrom. 25: 2307-2316.

Figure 10:
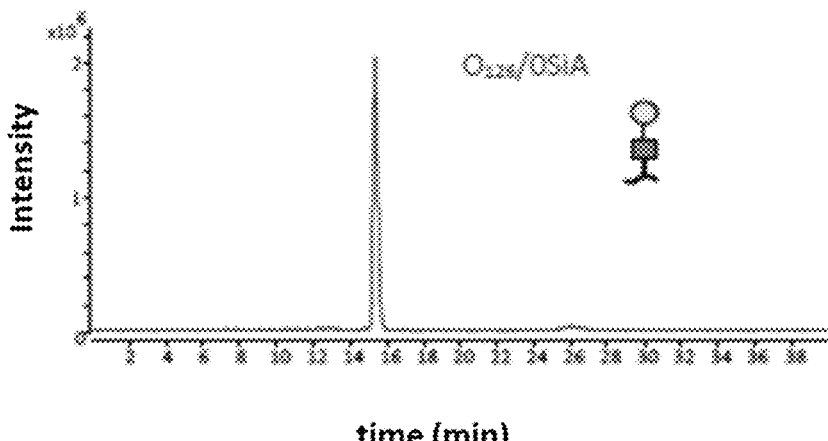
FIG. 10. Extracted ions electropherogram (EIE) of hyposialylated rhEPO 0126 glycopeptide glycoforms observed resulting from digestion with: a) trypsin and neuraminidase and b) trypsin.
Figure 10:
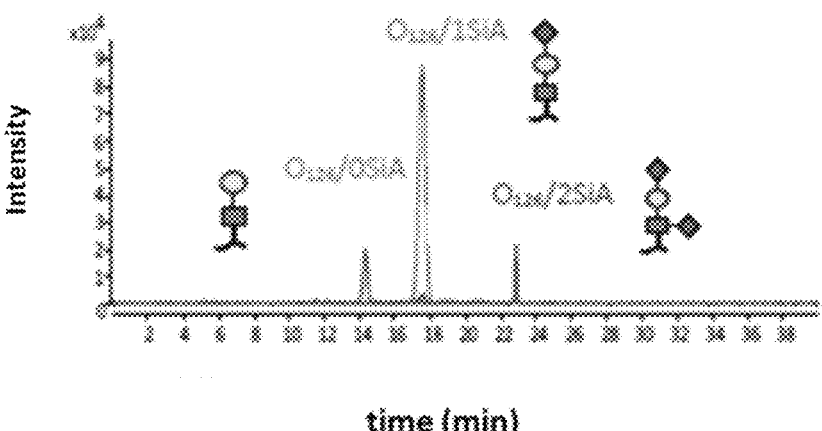

FIGS. 10A and B show the EIE of $O_{126}$ glycopeptide glycoforms detected in the rhEPO HS-TN and HS-T digestates, respectively. In the first one, a single peak corresponding to that of the $O_{126}$/0SiA glycoform is observed, since the neuraminidase produces a complete desialylation of the glycopeptide, so that all the sialoforms become a single glycoform. In contrast, when digested with trypsin only, three sialoforms with 0, 1 and 2 sialic acid molecules are observed.

Table 7 shows the $O_{126}$ sialoforms detected with the corresponding relative areas, monoisotopic experimental molecular mass (Mexp) and mass error.

TABLE 7

Glycoforms detected in $O_{126}$ glycopeptide of hyposialylated and CRS rhEPO digested with trypsin.

| | | rhEPO-CRS-T | | |
|---|---|---|---|---|
| Glycopeptide 0126 | Rt [min] | Rel Area [%] | Mexp[Da] | Error[ppm] |
| 0SiA | 12.1 | 1.61 | 1829.9169 | 15.0 |
| 1SiA | 14.6 | 60.4 | 2121.0166 | 15.0 |
| 2SiA | 18.4 | 38.0 | 2412.1175 | 15.0 |

TABLE 7-continued

Glycoforms detected in $O_{126}$ glycopeptide of hyposialylated and CRS rhEPO digested with trypsin.

| | | rhEPO-CRS-T | | |
|---|---|---|---|---|
| Glycopeptide 0126 | Rt [min] | Rel Area [%] | Mexp[Da] | Error[ppm] |
| | | hyposialylated-T EPO | | |
| 0SiA | 14.0 | 8.88 | 1829.9173 | 15.2 |
| 1SiA | 17.2 | 80.5 | 2121.0173 | 15.3 |
| 2SiA | 22.1 | 10.7 | 2412.1215 | 17.1 |

Figure 11:
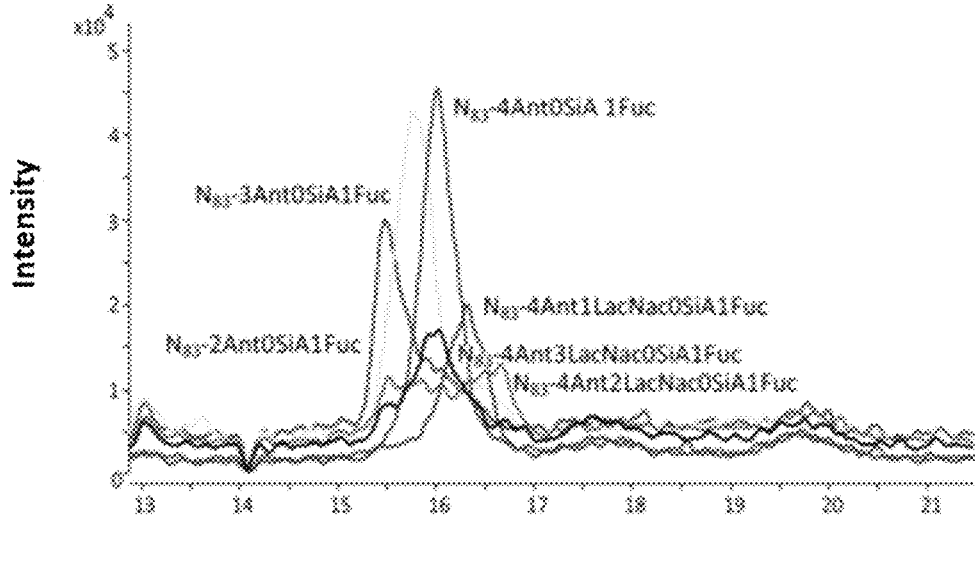
FIG. 11. EIE of N83 glycopeptide observed glycoforms resulting from trypsin and neuraminidase digestion.

The results obtained show that the most abundant sialoform is the one that contains one sialic acid molecule. Both the percentage of relative area of asialylated isoforms and of those with only one sialic acid are higher as compared to the ones described for other rhEPO, finding in the proportion of both sialoforms differences with the CRS rhEPO. In the case of the N83 glycopeptide, when analyzing the rhEPO HS-TN digest, six peaks were detected, corresponding to six different glycoforms without sialic acid. The EIEs obtained are shown in FIG. 11 and the detected glycoforms in Table 8. The results obtained show that in the $N_{83}$ site there is a higher percentage of complex desialylated tetraantennary structures.

TABLE 8

Detected glicoforms of EPO HS-TN $N_{83}$ glycopeptide

| Glycopeptide$_{83}$ | $R_t$[min] | Area$_{rel}$[%] | Mexp[Da] | Error[ppm] |
|---|---|---|---|---|
| 2Ant0SiA1Fuc | 15.4 | 17.12 | 4126.9263 | 13.0 |
| 3Ant0SiA1Fuc | 15.7 | 27.33 | 4492.0674 | 13.9 |
| 4Ant0SiA1Fuc | 15.9 | 24.30 | 4857.1996 | 12.9 |
| 4Ant1LacNAc0SiA1 | 16.2 | 12.50 | 5222.3335 | 12.3 |
| 4Ant2LacNAc0SiA1 | 16.4 | 6.75 | 5587.3257 | 13.6 |
| 4Ant3LacNAc0SiA1 | 15.9 | 12.0 | 5952.6219 | 14.8 |

Figure 12:
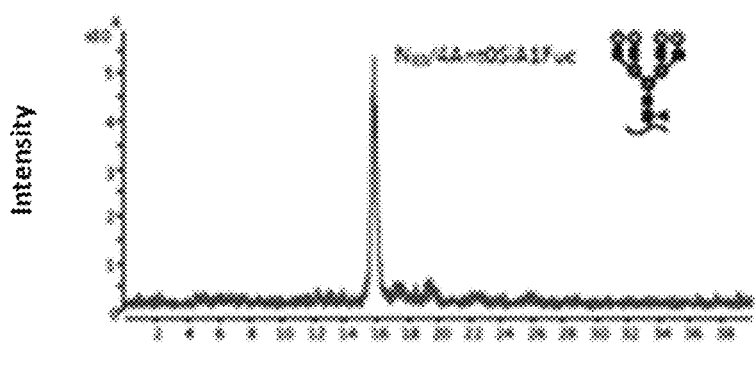
FIG. 12. EIE of hyposialylated rhEPO N83 glycopeptide observed glycoforms resulting from digestion with: a) trypsin and neuraminidase and b) trypsin.
Figure 12:
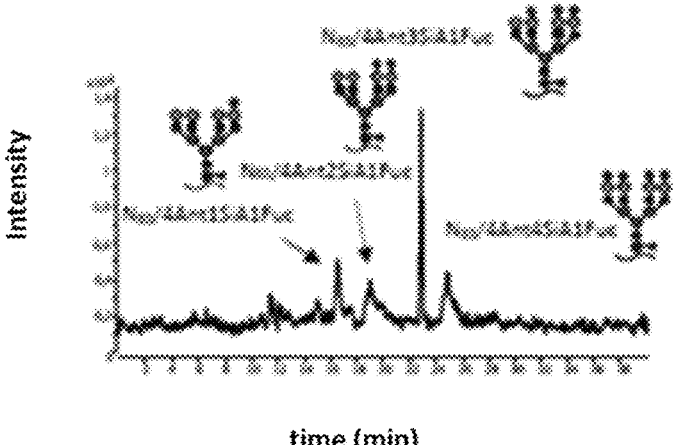

FIG. 12A shows that there is no separation between the different tetraantennary structures in the rhEPO HS-TN digestate. On the contrary, when the sialylated glycoforms of the rhEPO HS-T digestate are analyzed, a clear separation between them is observed, those with three sialic acid residues having greater intensity (FIG. 121B). These results agree with the findings from the study of glycans.

Table 9 shows all sialoformns detected and the corresponding relative areas, monoisotopic experimental molecular masses (Mexp) and mass error.

TABLE 9

Glycoforms of N83 glycopeptide detected in trypsin and trypsin/neuroaminidase digestates.

| | Glycopeptide $N_{83}$ | Ref area (%) | Area (%)** | Mexp[Da] | Error[ppm] |
|---|---|---|---|---|---|
| 2 Ant | 2Ant1SiA1Fuc | 2.54 | 10.47 | 4417.9833 | 3.43 |
| | 2Ant2SiA1Fuc | 7.93 | | 4709.1311 | 14.3 |
| 3Ant | 3Ant1SiA1Fuc | 9.17 | 19.56 | 4783.1079 | 1.58 |
| | 3Ant2SiA1Fuc | 7.49 | | 5074.2569 | 12.1 |
| | 3Ant3SiA1Fuc | 2.90 | | 5365.3564 | 12.2 |
| 4Ant | 4Ant1SiA1Fuc | 4.82 | 29.13 | 5148.2690 | 7.08 |
| | 4Ant2SiA1Fuc | 9.58 | | 5439.4017 | 13.6 |
| | 4Ant3SiA1Fuc | 9.06 | | 5730.5066 | 14.5 |
| | 4Ant4SiA1Fuc | 5.67 | | 6021.4347 | 14.0 |
| 4Ant 1LacAc | 4Ant1LacNAc1SiA1Fuc | 4.40 | 23.79 | 5513.3202 | 8.08 |
| | 4Ant1LacNAc2SiA1Fuc | 7.67 | | 5804.5468 | 14.9 |
| | 4Ant1LacNAc3SiA1Fuc | 5.96 | | 6095.5354 | 3.31 |
| | 4Ant1LacNAc4SiA1Fuc | 5.76 | | 6386.8708 | 34.4 |

TABLE 9-continued

Glycoforms of N83 glycopeptide detected in trypsin and trypsin/neuroaminidase digestates.

| Glycopeptide $N_{83}$ | | Ref area (%) | Area (%)** | Mexp[Da] | Error[ppm] |
|---|---|---|---|---|---|
| 4Ant | 4Ant2LacNAc2SiA1Fuc | 6.42 | 17.05 | 6169.8030 | 34.1 |
| 2LacAc | 4Ant2LacNAc3SiA1Fuc | 4.81 | 6460.6122 | 11.7 | |
| | 4Ant2LacNAc4SiA1Fuc | 5.82 | 6751.6217 | 23.9 | |

Results corroborate that the hyposialylated rhEPO is characterized by having less sialylated structures (for example, 2Ant1SiA1Fuc or 3Ant1SiA1Fuc) when the protein is digested only with trypsin. When the percentage of relative areas of the mono and bisialylated structures was verified, results show that they represent approximately 60%. The tetraantennary structures in the N83 glycopeptide, are found in the highest percentage as compared to other glycoforms, those with two sialic acid residues being the ones with the greatest proportion.

Example 9. Hyposialylated rhEPO has a Restorative Effect on Astrocytes Against the Cytotoxicity of DMSO PG4 astrocyte cell line was cultivated in Dulbecco's Modified Eagle's Medium (DMEM) culture medium high in glucose supplemented with 3.7 g/L $NaHCO_3$ and 10% fetal bovine serum (FBS). The cells were incubated for 24 hours at a temperature of 37° C. in an atmosphere of 5% $CO_2$/95% air. After the specified time the SN was extracted and the cells were subjected to damage caused with 8% DMSO and incubated again for 24 h. Subsequently, the SN was removed and 2% DMEM culture medium with different concentrations of hyposialylated rhEPO (1.25; 2.5; 5 and 10 ng/mL) was added. At 24 h and 48 h Alamar Blue reagent was added, then the cells were incubated for 6 h and a reading was made at 540/630 nm. All incubations were performed at a temperature of 37° C. in an atmosphere of 5% $CO_2$/95% air.

Figure 13:
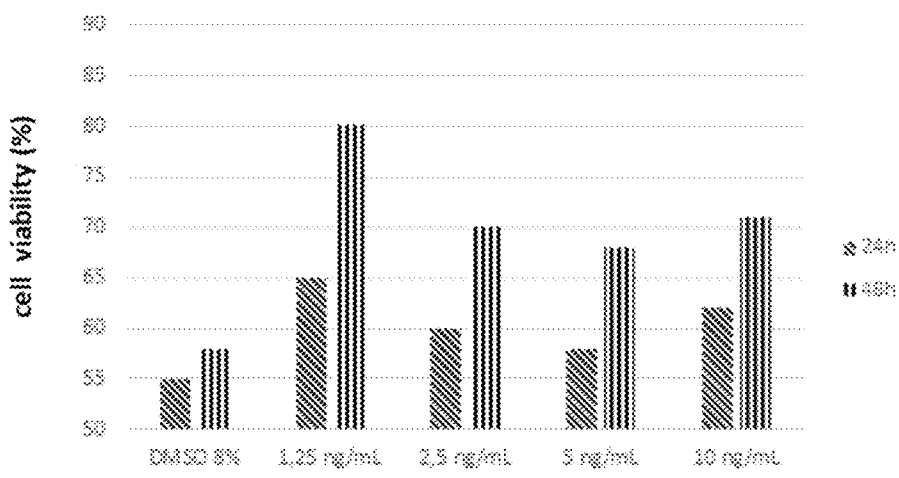
FIG. 13: Cell viability profile of the astrocyte culture at 24 and 48 hours after cell damage with 8% dimethylsulfoxide (DMSO) and subsequent treatment with hyposialylated rhEPO.

It can be seen in FIG. 13 how at the different concentrations 1.25; 2.5; 5 and 10 ng/mL of hyposialylated rhEPO the cells were able to regain their viability, the best condition being 1.25 ng/mL of hyposialylated rhEPO, which demonstrates the restorative capacity of astrocytes.

Example 10. Hyposialylated rhEPO has Better Neuroprotective Activity than NeuroEPO Gerbils from Mongolia were used to develop the model of permanent unilateral ischemia following the methodology described by Kahn K. in 1972, (Kahn K. (1972) Minneap 22: 510-515). Subsequently, the animals were randomized into five experimental groups:

Group 1: Vehicle 10 µL of the vehicle
Group 2: Treated with 0.142 mg/kg of hyposialylated rhEPO
Group 3: Treated with 0.0142 mg/kg of hyposialylated rhEPO
Group 4: Treated with 0.142 mg/kg of NeuroEPO
Group 5: Treated with 0.0142 mg/kg of NeuroEPO Each treatment was administered by IN route, three times a day for four days. The animals were evaluated during the first 4 days of treatment, as well as during recovery the next 3 days.

Figure 14:
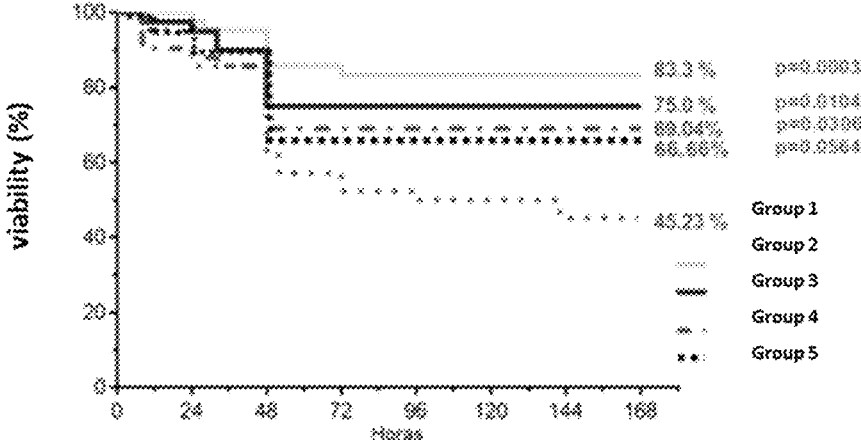
FIG. 14. Kaplan-Meier chart, viability during the 7 days of observation.

The results show a significantly greater survival rate of the animals treated with the hyposialylated rhEPO in the doses of 0.142 and 0.0142 mg/kg when compared with the vehicle, while the NeuroEPO only decreased mortality significantly in the dose 0.142 mg/kg but not in the 0.0142 mg/kg (FIG. 14).

Figure 15:
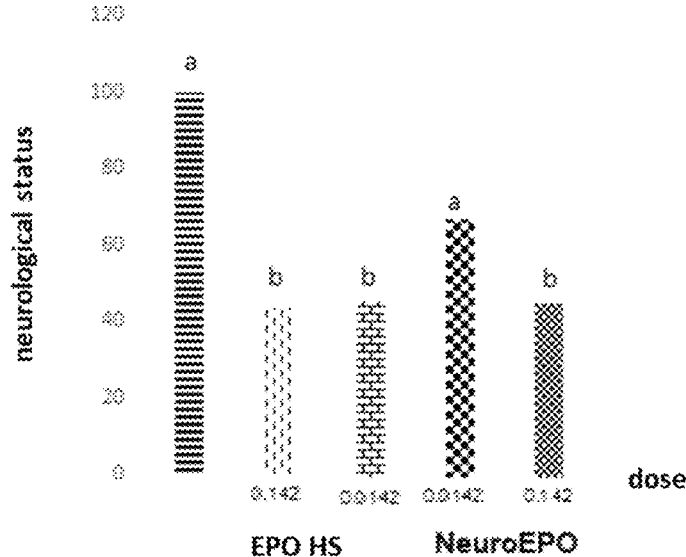
FIG. 15. Neurological status of animals at 24 hours after infarction.

The neurological evaluation showed the neuroprotective effect of hyposialylated rhEPO (NeuroEPO plus), which significantly decreased the values of the neurological scale in the animals treated with it in the doses used, as compared with the placebo group and with the groups treated with NeuroEPO, in which the same result obtained with hyposialylated rhEPO could only be achieved with the 0.142 mg/kg dose. (FIG. 15). (Duncan statistical test, equal letters p>0.05; different letters p>0.05).

Example 11 Hyposialylated rhEPO does not Increase the Reticulocyte Count in the Normocytemic Mouse Model B6D2F1 female mice were randomized into 6 experimental groups of 6 animals each and received a single dose of treatment as follows:

Group 1: 0.003 mg/mL of rhEPO working reference material in a 200 µL volume by subcutaneous route (SC).
Group 2: 0.006 mg/mL of hyposialylated rhEPO in a 200 µL volume by SC route.
Group 3: 0.5 mg/mL of hyposialylated rhEPO in a 200 µL volume by IN route.
Group 4: 1 mg/mL of hyposialylated rhEPO in a 200 µL volume by IN route.
Group 5: 2 mg/mL of hyposialylated rhEPO in a 200 µL volume by IN route.
Group 6: Control, 200 µL excipient by SC route.

Figure 16:
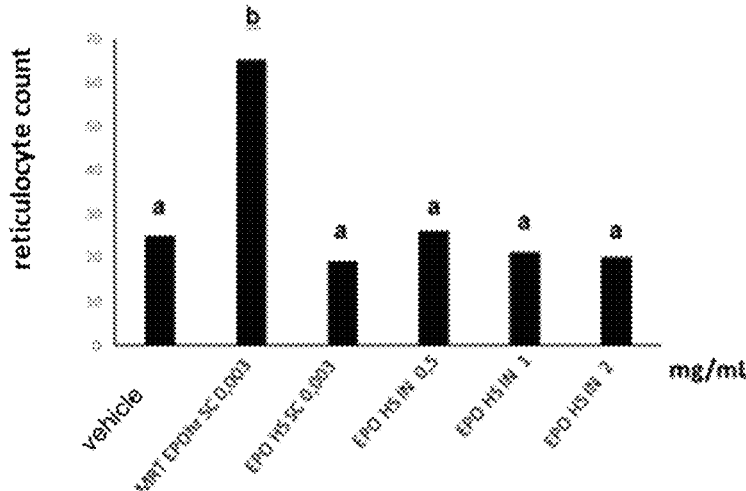
FIG. 16. Effect of the application of different rhEPO isoforms on the number of reticulocytes in the normocytemic mouse model.

The results of the reticulocyte count are shown in FIG. 16. As can be seen there were no significant differences between the animals in the control group and those in the groups treated with hyposialylated rhEPO both by SC and IN. The reticulocyte count of the animals treated with the rhEPO work reference material was significantly higher than the one of the animals in the control group and in the group treated with hyposialylated rhEPO, with both routes used. (Duncan test, equal letters p>0.05; different lettersp<0.05).

The results demonstrated that hyposialylated EPO does not increase the reticulocyte count even at the highest dose established for this trial, which shows that it has no hematopoietic effect.

The invention claimed is:

1. A pharmaceutical composition comprising as active ingredient a recombinant human erythropoietin (rhEPO) whose isoelectric point profile is between 4.25 and 5.85 and having O-glycosylation and N-glycosylation sites wherein a microheterogeneity of fucosylated N-glycans is formed by bi, tri and tetra-antennary structures, which have mono and bi-sialylated sialic acid residues in a range of 40-60% of total glycans, tri-sialylated residues in a range from 40-43% of total glycans and tetrasialylated residues in a range from 10-13% of total glycans; and said composition further comprising a pharmaceutically acceptable excipient.

2. The pharmaceutical composition of claim 1 wherein an O-glycosylation site in serine 126 has 3 sialoforms that have between 0 and 2 sialic acid residues, where a monosialylated structure is most abundant and represents between 78-82% of total glycans and asialylated structures represent between 6-10% of total glycans.

3. The pharmaceutical composition of claim 1 wherein an N-glycosylation site of asparagine 83 comprises:

Fucosylated biantennary structures with 1 and 2 sialic acid residues, wherein said structures represent 8-12% of the total glycans, Fucosylated triantennary structures with 1, 2 and 3 sialic acid residues, wherein said structures represent 17-21% of the total glycans, Fucosylated tetraantennary structures with between 1 and 4 sialic acid residues, wherein said structures represent 27-31% of total glycans and Fucosylated tetraantennary structures with N-acetyl lactosamine type 1 and 2 that present between 1 to 4 sialic acid residues, wherein said structures represent 38-42% of total glycans.

4. The pharmaceutical composition of claim 1 wherein the pharmaceutically acceptable excipient comprises bioadhesive polymers and protein stabilizers.

5. The pharmaceutical composition of claim 4 wherein the bioadhesive polymers are selected from the group consisting of:

hydroxymethylcellulose, hydroxypropylcellulose and methylcellulose.

6. The pharmaceutical composition of claim 4 wherein the protein stabilizers are selected from the group consisting of:

L-tryptophan,

L-leucine,

L-arginine hydrochloride and

L-histidine hydrochloride.

\* \* \* \* \*